United States Patent
Ladel et al.

(10) Patent No.: US 10,086,112 B2
(45) Date of Patent: Oct. 2, 2018

(54) IMPLANT COMPRISING FGF-18

(71) Applicant: MERCK PATENT GMBH, Darmstadt (DE)

(72) Inventors: Christoph H. Ladel, Darmstadt (DE); Hans Guehring, Eltville (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/120,137

(22) PCT Filed: Feb. 20, 2015

(86) PCT No.: PCT/EP2015/053645
§ 371 (c)(1),
(2) Date: Aug. 19, 2016

(87) PCT Pub. No.: WO2015/124739
PCT Pub. Date: Aug. 27, 2015

(65) Prior Publication Data
US 2017/0056560 A1    Mar. 2, 2017

(30) Foreign Application Priority Data
Feb. 20, 2014 (EP) .................... 14000598

(51) Int. Cl.
| A61K 38/16 | (2006.01) |
|---|---|
| A61K 38/17 | (2006.01) |
| A61K 38/18 | (2006.01) |
| A61K 38/39 | (2006.01) |
| A61L 27/54 | (2006.01) |
| A61L 27/24 | (2006.01) |
| A61L 27/26 | (2006.01) |
| A61L 27/22 | (2006.01) |
| A61L 27/38 | (2006.01) |

(52) U.S. Cl.
CPC .......... *A61L 27/54* (2013.01); *A61K 38/1825* (2013.01); *A61L 27/22* (2013.01); *A61L 27/24* (2013.01); *A61L 27/26* (2013.01); *A61L 27/3817* (2013.01); *A61L 2300/414* (2013.01); *A61L 2430/06* (2013.01)

(58) Field of Classification Search
None
See application file for complete search history.

(56) References Cited

U.S. PATENT DOCUMENTS

| 6,511,958 B1 | 1/2003 | Atkinson et al. | |
|---|---|---|---|
| 2006/0172384 A1* | 8/2006 | Reardon | C07K 14/501 435/69.1 |
| 2008/0213333 A1 | 9/2008 | Vignery et al. | |
| 2010/0247651 A1* | 9/2010 | Kestler | A61K 38/1858 424/484 |
| 2013/0288972 A1* | 10/2013 | Chen | C07K 14/78 514/16.8 |
| 2013/0325144 A1 | 12/2013 | Benkirane-Jessel et al. | |

FOREIGN PATENT DOCUMENTS

| WO | WO 2004/032849 | 4/2004 |
|---|---|---|
| WO | WO 2015097236 A2 * | 7/2015 |
| WO | WO 2015/124727 | 8/2015 |
| WO | WO 2015/124731 | 8/2015 |
| WO | WO 2015/124735 | 8/2015 |

OTHER PUBLICATIONS

Moore et al. Fibroblast growth factor-18 stimulates chondrogenesis and cartilage repair in a rat model of injury-induced osteoarthritis. Osteoarthritis Cartilage. Jul. 2005;13(7):623-31.*
Written Opinion in International Application No. PCT/EP2015/053645, dated May 6, 2015, pp. 1-5.

* cited by examiner

*Primary Examiner* — Elizabeth Kemmerer
(74) *Attorney, Agent, or Firm* — Saliwanchik, Lloyd & Eisenschenk (57) ABSTRACT

The invention relates to the field of pharmaceutical compositions. More particularly it is directed to substance delivery system (or implant), such as scaffolds and membranes, comprising an anabolic drug, such as a Fibroblast Growth Factor 18 (FGF-18) compound, to methods of producing such delivery system, as well as use thereof. The implants according to the invention are for use for the treatment of cartilage disorders, such as osteoarthritis, cartilage injury or osteochondral defects.

11 Claims, 5 Drawing Sheets
Specification includes a Sequence Listing.

IMPLANT COMPRISING FGF-18

CROSS-REFERENCE TO RELATED APPLICATION

This application is the U.S. national stage application of International Patent Application No. PCT/EP2015/053645, filed Feb. 20, 2015.

The Sequence Listing for this application is labeled "Seq-List.txt" which was created on Aug. 2, 2016 and is 5 KB. The entire content of the sequence listing is incorporated herein by reference in its entirety.

FIELD OF INVENTION

The invention relates to the field of pharmaceutical compositions. More particularly it is directed to substance delivery system (or implant), such as scaffolds and membranes, comprising an anabolic drug, such as a Fibroblast Growth Factor 18 (FGF-18) compound, to methods of producing such delivery system, as well as use thereof. The implants according to the invention are for use for the treatment of cartilage disorders, such as osteoarthritis, cartilage injury or osteochondral defects.

BACKGROUND OF THE INVENTION

Fibroblast Growth Factor 18 (FGF-18) is a member of the Fibroblast Growth Factor (FGF) family of proteins, closely related to FGF-8 and FGF-17. Members of the FGF family are characterized by heparin binding domains. Such a putative heparin-binding domain has been identified for FGF-18. It is postulated that receptor-mediated signalling is initiated upon binding of FGF ligand complexed with cell-surface heparin sulfate proteoglycans. It has been shown that FGF-18 is a proliferative agent for chondrocytes and osteoblasts (Ellsworth et al., 2002; Shimoaka et al., 2002). FGF-18 has been proposed for the treatment of cartilage disorder such as osteoarthritis (OA) and cartilage injury (CI) either alone (WO2008/023063) or in combination with hyaluronic acid (WO2004/032849).

Pharmaceutical compositions comprising an FGF polypeptide are known in the art. WO2012172072 describes a freeze-dried formulation containing FGF-18, wherein said composition comprises FGF-18, a buffer, a poloxamer surfactant and a sugar as stabilizing agent. Said FGF-18 freeze-dried formulation is showing promising results in the treatment of OA or CI. The current dosing regimen, using said freeze-dried formulation, is a treatment cycle of once weekly injection for 3 weeks. The treatment cycle can be repeated.

The main drawback of the current FGF-18 formulation is that, once injected intraarticularly (i.e.), the presence of FGF-18 in the synovial fluid may also induce uncontrolled cartilage growth in healthy areas. This can induce, of course, unwanted effects such as reduced joint mobility. The delivery of FGF-18 selectively at the level of the target site could promote the cartilage growth only in the damaged area. In particular, the delivery of FGF-18 at the level of the damaged area could be highly beneficial for the treatment of OA or CI, notably when coupled with microfracture. Microfracture is an articular cartilage repair surgical technique that works by creating small fractures in the underlying bone. This causes the release of pluripotent mesenchymal stem cells from the bone marrow (Ringe J. et al., 2012). Filling the cartilage hole with a scaffold or a membrane containing FGF-18 would direct cells within said matrix that would, then, act as mechanical supports for cell growth and drug reservoirs at the same time. For this reason, it would be preferable if FGF-18 is slowly released from the scaffold/membrane to the surrounding tissue and/or stays entrapped in the scaffold/membrane.

A typical approach in tissue engineering is the confinement of growth factors in a 3D matrix, i.e. on a scaffold or membrane, that can be either implanted or injected, depending on its mechanical properties, in order to assume the shape of the acceptor site (Yun et al., 2010). Mandatory characteristics of the scaffolds/membranes are biocompatibility and resorbability. Additionally, scaffolds/membranes must be able to provide cells with the ideal environment to grow, proliferate and reform the damaged tissue. Ideally, the matrix should resemble the same mechanical properties as the original tissue and should present a microporosity able to host cells (interconnected pores with a sufficient size) (Tessmar and Gopferich, 2007).

Some matrices useful for tissue engineering are already commercialized. For instance, Chondro-Gide™ membrane (Geistlich Biomaterials) consists of collagen types I and III, arranged in a bilayer structure. This membrane has been approved in some countries, for instance in France, in combination with autologuous chondrocyte implantation (preferably in combination with the approved product ChondroCelect™). A similar product, Maci (Genzyme), has been recently approved in the European market. It consists of autologous chondrocytes expanded ex vivo expressing chondrocyte-specific marker genes, seeded onto a Type I/III collagen membrane (Maix). Chondromimetic™ (Orthomimetics Ltd.) is a scaffold composed of type I bovine collagen and chondroitin-6-sulphate glycosaminoglycan (collagen/GAG scaffold). This implant has also been approved for the European market.

For instance, WO2012113812 describes nanofibrous scaffold functionalized via coating with polyelectrolyte multilayers, i.e. at least one layer of polyanions and one layer of polycations. Therapeutic molecules, such as FGF-18, can be included in the polyelectrolyte multilayers. In particular, the therapeutic molecule can form the polyanion layer. Said scaffold may optionally further comprising osteoblasts within a collagen hydrogel and chondrocytes within an alginate hydrogel, each hydrogel being deposited on the coated scaffold. Said scaffold is to be implanted in situ, via surgery.

When preparing a pharmaceutical composition comprising a bioactive protein, said composition must be formulated in such a way that the activity of the protein is maintained for an appropriate period of time. A loss in activity/stability of the protein may result from chemical or physical instabilities of the protein notably due to denaturation, aggregation or oxidation. The resulting products may thus be pharmaceutically unacceptable. Although the use of excipient(s) and/or matrix is known to increase the stability of a given protein, the stabilizing effects of these excipients is highly dependent on the polymer in the matrix, the nature of the excipients, if any, and the bioactive protein itself.

Although tissue engineering procedures are promising, integration rate or quality of the cartilage produced has to be improved. There is therefore a need of an improved composition, allowing good integration and good quality of the cartilage produced (i.e. mainly hyaline cartilage); there is also a need for an alternative system to provide a therapeutic compound to the site of defect. Indeed, generation of said hyaline cartilage is valuable both as a therapeutic and as a component for biological matrices (Power et al., 2012). Said compositions could be useful in the frame of tissue engineering procedures for the treatment of a cartilage disorder in a patient, such as osteoarthritis, cartilage injury or osteochondral defects.

SUMMARY OF THE INVENTION

Herein described is a substance delivery system comprising at least one polymeric material forming a matrix and an anabolic drug, wherein said anabolic drug is included in the at least one polymeric material forming the matrix. Said matrix is preferably a scaffold or a membrane. In a particular embodiment, the scaffold is a biphasic scaffold or the membrane is a bilayered membrane. Preferably, the at least one polymeric material is collagen. Alternatively, the at least one polymeric material is a combination of collagen and glycosaminoglycan (GAG). The anabolic drug, contained in the delivery system, is preferably an FGF-18 compound. In a particular embodiment of the invention, the FGF-18 compound is selected from the group consisting of: a) a polypeptide comprising or consisting of the human FGF-18 mature form comprising residues 28-207 of SEQ ID NO:1, or b) a polypeptide comprising or consisting of SEQ ID NO:2.

The substance delivery system according to the present invention can further comprise chondrogenic cells, including mesenchymal stem cells. Preferably, such chondrogenic cells are chondrocytes. In particular, the chondrogenic cells, such as chondrocytes or mesenchymal stem cells, are harvested or isolated from the patient in need of a treatment or from a different donor (preferably belonging to the same species).

In another embodiment, the invention provides a process for producing the substance delivery system according to the present invention, which comprises the steps of: a) preparing a matrix comprising at least one polymeric material, and b) adding the anabolic drug to the matrix prepared in step a) wherein said anabolic drug is included in the at least one polymeric material forming the matrix. Alternatively, said process further comprises the step c) adding chondrogenic cells to the matrix prepared in step a).

In a further embodiment, the substance delivery system herein described is for use in the treatment of a cartilage disorder. The cartilage disorder is preferably selected from osteoarthritis, cartilage injury and osteochondral defects.

The substance delivery system according to the invention is preferably administered to a patient in need of said treatment via a transplantation procedure.

In a yet further embodiment, herein described is an article of manufacture comprising the substance delivery system according to the invention. Preferably, the components of said article of manufacture are combined extemporaneously. Alternatively, the components of said article of manufacture are combined either before or after implantation.

Definitions

The term "anabolic compound" or "anabolic drug" is to be understood as a compound or a drug that has anabolic effects on the cartilage, preferably leading to cartilage repair. In the context of the present invention, an "anabolic compound" or "anabolic drug" is preferably a therapeutic protein, having an anabolic effect on the cartilage. Among such compounds, or therapeutic proteins, the preferred compound is an FGF-18 compound (as defined herein).

The term "FGF-18 compound" or "FGF-18", as used herein, is intended to be a protein maintaining at least one biological activity of the human FGF-18 protein. FGF-18 may be native, in its mature form, a recombinant form or a truncated form thereof. Biological activities of the human FGF-18 protein include notably the increase in chondrocyte or osteoblast proliferation (see WO98/16644) or in cartilage formation (see WO2008/023063). Native, or wild-type, human FGF-18 is a protein expressed by chondrocytes of articular cartilage. Human FGF-18 was first designated zFGF-5 and is fully described in WO98/16644. SEQ ID NO:1 corresponds to the amino acid sequence of the native human FGF-18, with a signal peptide consisting of amino acid residues 1(Met) to 27(Ala). The mature form of human FGF-18 corresponds to the amino acid sequence from residue 28(Glu) to residue 207(Ala) of SEQ ID NO: 1 (180 amino acids).

FGF-18, in the present invention, may be produced by a recombinant method, such as taught by WO2006/063362. Depending on the expression systems and conditions, FGF-18 in the present invention is expressed in a recombinant host cell with a starting Methionine (Met) residue or with a signal sequence for secretion. When expressed in prokaryotic host, such as in *E. coli*, FGF-18 contains an additional Met residue in N-terminal of its sequence. For instance, the amino acid sequence of human FGF-18, when expressed in *E. coli*, starts with a Met residue in N-term (position 1) followed by residues 28 (Glu) to residue 207 (Ala) of SEQ ID NO: 1.

The term "truncated form" of FGF-18, as used herein, refers to a protein which comprises or consists of residues 28(Glu) to 196(Lys) of SEQ ID NO: 1. Preferably, the truncated form of FGF-18 protein is the polypeptide designated "trFGF-18" (170 amino acids; also known as rhFGF-18 or sprifermin), which starts with a Met residue (in N-terminal) followed by amino acid residues 28 (Glu)-196 (Lys) of the wild-type human FGF-18. The amino acid sequence of trFGF-18 is shown in SEQ ID NO:2 (amino acid residues 2 to 170 of SEQ ID NO:2 correspond to amino acid residues 28 to 196 of SEQ ID NO:1). trFGF-18 is a recombinant truncated form of human FGF-18, produced in *E. coli* (see WO2006/063362). trFGF-18 has been shown to display similar activities as the mature human FGF-18, e.g. it increases chondrocyte proliferation and cartilage deposition leading to repair and reconstruction for a variety of cartilaginous tissues (see WO2008/023063).

The term "homogeneous" means that the various components of the formulation are mixed, blended, stirred or melted together, i.e., they do not form separate layers of components.

The term "cartilage disorder", as used herein, encompasses disorders resulting from damages due to injury, such as traumatic injury, chondropathy or arthritis. Examples of cartilage disorders that may be treated by the administration of the FGF-18 formulation described herein include but are not restricted to arthritis, such as osteoarthritis, cartilage injury and osteochondral defects. Degenerative diseases/disorders of the cartilage or of the joint, such as chondrocalcinosis, polychondritis, relapsing polychondritis, ankylosing spondylitis or costochondritis are also encompassed by this wording. The International Cartilage Repair Society has proposed an arthroscopic grading system to assess the severity of the cartilage defect: grade 0: (normal) healthy cartilage, grade 1: the cartilage has a soft spot or blisters, grade 2: minor tears visible in the cartilage, grade 3: lesions have deep crevices (more than 50% of cartilage layer) and grade 4: the cartilage tear exposes the underlying (subchronal) bone (see the publication from ICRS: Worldwide Website: cartilage.org/_files/contentmanagement/ICRS_evaluation.pdf, page 13).

The term "arthritis" as used herein encompasses disorders such as osteoarthritis, rheumatoid arthritis, juvenile rheumatoid arthritis, infectious arthritis, psoriatic arthritis, Still's disease (onset of juvenile rheumatoid arthritis) or osteochondritis dissecans. It preferably includes diseases or disorders in which ones the cartilage is damaged.

The term "Osteoarthritis" is used to intend the most common form of arthritis. The term "osteoarthritis" is considered as a cartilage disorder which encompasses both primary osteoarthritis and secondary osteoarthritis (see for instance The Merck Manual, 17$^{th}$ edition, page 449). Osteoarthritis may be caused by the breakdown of cartilage. Bits of cartilage may break off or degradation fragments of cartilage components (like collagen type II, Aggrecan) can leak off the joint and cause pain and swelling in the joint between bones in the articulation. Over time, the cartilage may wear away entirely, and the bones will rub together. Osteoarthritis can affect any joint but usually concerns hands and weight-bearing joints such as hips, knees, feet, and spine. In a preferred example, the osteoarthritis may be knee osteoarthritis or hip osteoarthritis. This wording encompasses notably the forms of osteoarthritis which are classified as stage 1 to stage 4 or grade 1 to grade 6 according to the OARSI classification system. The skilled person is fully aware of osteoarthritis classifications that are used in the art, in particular said OARSI assessment system (also named OOCHAS; see for instance Custers et al., 2007). Osteoarthritis is one of the preferred cartilage disorders that can be treated by administering the FGF-18 compounds according to the present invention.

The term "cartilage injury" as used herein is a cartilage disorder or cartilage damage resulting notably from a trauma. Cartilage injuries can occur notably after traumatic mechanical destruction, notably further to an accident or surgery (for instance microfracture surgery). The term "cartilage injury" also includes chondral or osteochondral fracture and damage to meniscus. Also considered within this definition is sport-related injury or sport-related wear of tissues of the joint. The term also includes microdamage or blunt trauma, a chondral fracture, an osteochondral fracture or damage to meniscus.

The term "osteochondral defects" (OCD) is a cartilage disorder in which defects of the cartilage cover the end of a bone in a joint. These defects are most often due to trauma or injury, but can also be due to a pathology. OCD may lead to OA.

The term "matrix" refers to a 3-dimensional (3D) structure, such as membrane or scaffold. Such matrix can be used as an "implant" or as a "substance delivery system", or "delivery system" when the matrix, or implant, further comprises the anabolic drug (i.e. the therapeutic protein having an anabolic effect on cartilage to be delivered). The terms "implant", "substance delivery system", or "delivery system" are herein interchangeable.

The terms "implantation" and "transplantation" are interchangeable. Similarly, the terms "implanting", "transplanting" and "disposing the system" are interchangeable.

The term "slow release" according to the present invention means that low amounts of a given compound, such as FGF-18 compound, are released over a period of at least 4 weeks and more.

DETAILED DESCRIPTION OF THE INVENTION

Although cartilage restorative procedures making use of matrices, or implants, are promising, the quality of the cartilage produced has to be improved. There is therefore a need for an improved delivery system, allowing good integration and good quality of the cartilage produced (i.e. mainly hyaline cartilage). It has been surprisingly found that when FGF-18 is used in a matrix, such as a collagen membrane or a collagen/glycosaminoglycan scaffold, it produces a superior repair tissue to a matrix alone or a matrix combined with a different protein.

The main object of the present invention is therefore a substance delivery system comprising at least one polymeric material forming a matrix and an anabolic drug, wherein said anabolic drug is included in the at least one polymeric material forming the matrix. Said matrix is suitable for introduction at the cartilage level. The substance delivery system according to the present invention can further comprise chondrogenic cells. The substance delivery system may also further comprise other excipients or other components. The advantage of the use of such delivery system is the possibility to introduce the implant, already containing an anabolic compound, directly into the cartilage or osteochondral defect. Alternatively, the anabolic drug and/or the chondrogenic cells, if any, can be introduced into the implant once this one has been implanted in the defect.

In another embodiment, the invention provides a process for producing the substance delivery system, or implant, according to the present invention, which comprises the steps of: a) preparing a matrix comprising at least one polymeric material, and b) adding the anabolic drug to the matrix prepared in step a) wherein said anabolic drug is included in the at least one polymeric material forming the matrix. Alternatively, said process further comprises the step c) adding chondrogenic cells to the matrix prepared in step a). Any one of steps b) and c) can be performed either before implantation or after implantation (i.e. in situ) in the defect.

In a yet further embodiment, herein described is an article of manufacture comprising the substance delivery system according to the invention. Preferably, the components of said article of manufacture are combined extemporaneously. Alternatively, the components of said article of manufacture are combined either before or after implantation. Also described is a packaging material providing instructions to form the delivery system according to the present invention.

In the context of the present invention as a whole, the matrix (or implant) is preferably a scaffold or a membrane. In a particular embodiment, the scaffold is a biphasic scaffold or the membrane is a bilayered membrane. Preferably, the at least one polymeric material is collagen. Alternatively, the at least one polymeric material is a combination of collagen and glycosaminoglycan (GAG). The matrix can be a matrix already available on the market, such as Chondro-Gide™ membrane, a Chondromimetic™ scaffold, or any other commercially available matrix (either approved or not yet approved by regulatory agencies). Alternatively, the matrix can be made in-house.

The anabolic drug (i.e. the therapeutic protein having anabolic effects on cartilage), contained in the delivery system (i.e. included in the at least one polymeric material forming the matrix), is preferably an FGF-18 compound. In a particular embodiment of the invention, the FGF-18 compound is selected from the group consisting of: a) a polypeptide comprising or consisting of the human FGF-18 mature form comprising residues 28-207 of SEQ ID NO:1, or b) a polypeptide comprising or consisting of SEQ ID NO:2. Particularly, this compound is selected from human wildtype mature FGF-18 or trFGF-18. More preferably, the FGF-18 compound is sprifermin.

In the context of the present invention, the anabolic drug, such as an FGF-18 compound, is added into the delivery system at a dose of or of about 0.05 to 200 mcg/system, preferably of or of about 0.5 to 100 mcg/system, more preferably of or of about 1, 5, 6, 10, 15, 20, 25, 30, 32, 35, 40, 45, 50, 55, 60, 65, 70, 75, 80, 85, 90, 95, 100, 110, 150 or 200 mcg/system, even more preferably of or of about 5, 6, 10, 20, 30, 32, 40, 50, 60, 70, 80, 90 or 100 mcg/system.

When chondrogenic cells are added into the delivery system, such chondrogenic cells are preferably chondrocytes. In particular, the chondrogenic cells, such as chondrocytes, are harvested or isolated from a mammal, and expanded in a culture medium before being implanted together with the matrix (addition of the cells either before or after implantation). In a particular embodiment, the culture medium in which the cells are expanded can comprise an anabolic compound, such as FGF-18 compound. In such a case, the anabolic compound is preferably added intermittently in the culture or storage medium, for about one day per week, said one-day addition being repeated each week for at least 2 weeks of culture, at least 3 weeks of culture or at least 4 weeks of culture. Preferably, said anabolic compound is added intermittently in the culture or storage medium, for one day per week, said one-day addition being repeated each week for 2 weeks of culture, 3 weeks of culture or 4 weeks of culture. Alternatively, the anabolic drug can be added intermittently in the culture or storage medium, for about one day per month, said one-day addition being repeated each month for at least 2 months of culture, at least 3 months of culture or at least 4 months of culture. Preferably, the anabolic drug is added intermittently in the culture or storage medium, for one day per month, said one-day addition being repeated each month for 2 months of culture, 3 months of culture or 4 months of culture.

The mammal is preferably the patient in need of treatment or a different donor (preferably belonging to the same species). Said mammal is more particularly a human. However, it can also be mammal such as, and without any limitation, a horse, a sheep, a dog, a cat, a rabbit, a rat or a mouse.

The substance delivery system herein described is preferably for use in the treatment of a cartilage disorder. Alternatively, herein disclosed is a method for the treatment of a cartilage disorder which comprises the step of administering the substance delivery system according to the present invention. Alternatively, also encompassed is a method for the treatment of a cartilage disorder which comprises the step of administering an implant according to the present invention, wherein the anabolic drug, such as an FGF-18 compound, and/or the chondrogenic cells are added into said implant either before or after implantation. The cartilage disorder is preferably selected from osteoarthritis, cartilage injury and osteochondral defects.

The substance delivery system according to the invention is preferably administered to a patient in need of said treatment via implanting or transplanting or otherwise disposing the system into the effect or into a site in need of articular cartilage repair, regeneration or growth.

The following examples are provided to further illustrate the invention. The scope of the invention shall not be construed as merely consisting of the following examples.

DESCRIPTION OF THE SEQUENCES

SEQ ID NO:1: Amino acid sequence of the native human FGF-18.

SEQ ID NO:2: Amino acid sequence of the recombinant truncated FGF-18 (sprifermin).

SEQ ID NO:3: Amino acid sequence of the recombinant BMP-7 (also known as eptotermin alfa).

EXAMPLES

Material

The recombinant truncated FGF-18 (rhFGF-18) of the present examples has been prepared by expression in *E. coli*, according to the technique described in WO2006/063362. In the following examples, rhFGF-18, FGF-18 and sprifermin are used interchangeably.

Methods

Gait analysis: A force plate (Accusway, AMTI, USA) was used to quantify the weight bearing of the operated limb. Weight-bearing was measured at a walking gait prior to surgery and 2 weeks, 4 weeks, 2 months, 3 months, 4 months and 5 months after surgery. At each time point each animal had a total of 10 recordings acquired at a walking gait to allow a mean weight bearing value to be calculated. Each measurement was converted into N/kg force and calculated as a percentage of weight bearing measured acquired prior to surgery for each animal. Weight bearing data was grouped into treatment groups for final analysis.

Gross Morphology: The joints were opened, photographed and the surface of the osteochondral defect sites blindly scored using the International Cartilage Repair Society (ICRS) score (Table 3).

Mechanical testing: After the gross morphological observations were made, each implant site underwent non-destructive mechanical testing to determine changes to the cartilage surface surrounding the implant or empty defect. Stiffness measurements were taken in duplicate from the centre of the osteochondral defect, and at a distance of 1 mm from the original edge of the created osteochondral defect at the 12, 3, 6, and 9 o'clock positions, and 1 mm from the edge in the perilesional cartilage, using a handheld digital durometer (Shore S1, M scale, Instron Ltd, UK). A number between 0-100 would be given with an inbuilt calibrated error of +/−5. These measurements were then repeated in the contralateral limb in the same anatomical sites.

Histology:

Following stiffness measurements the specimens were decalcified in formic acid/sodium citrate over two weeks. Following complete decalcification, the specimens were dehydrated through a series of ethanol exchanges of increasing concentrations, and then embedded in paraffin wax. Sections of 10 µm thickness were made through the central portion of the defect. Sections were stained with Toluidine Blue and Safranin O/Fast Green. The histology sections were blindly scored by one investigator, using a modified O'Driscoll score (Table 4). The animals that scored the best and the median total modified O'Driscoll scores within their experimental group were then identified and immunohistochemically performed on these sections. In addition to the total modified O'Driscoll score the individual components of the scoring system were analysed separately.

Immunohistochemistry: The following primary antibodies were used in this study: monoclonal mouse anti human type I collagen (MP Biomedicals, US), monoclonal mouse anti human type II collagen (MP Biomedicals, US) and monoclonal mouse anti-rabbit type VI collagen (Abcam, UK). Horseradish peroxidase-conjugated secondary anti-rabbit and mouse immunoglobulins were used as appropriate, and the colour reaction developed with 0.1% 3',3-diaminobenzidine tetrachloride (DAB)/0.01% hydrogen peroxide. Normal species-specific serum was used as a control in all experiments.

Statistical Analysis:

GraphPad Prism 5 statistical software package (Graphpad Software Inc, La Jolla, Calif.) was used for data analysis. Statistical significance between groups and within groups for each end point was mainly determined using a non-parametric Kruskal-Wallis test, with a post hoc Dunn's multiple comparison test. In one instance a one-way ANOVA test with post hoc Tukey's multiple comparison test was used. A level of $p<0.05$ was accepted as significant in all analyses.

Example 1: Collagen Scaffold Comprising rhFGF-18

Method

Thirty-five skeletally mature Welsh Mountain Sheep between the ages of 3 and 5 years old have been included in the study. The animals have been dispatched in 7 treatment groups, two of which acted as controls (Table 1). Prior to surgery, all animals have been anaesthetised with a mixture of isoflurane, nitrous oxide and oxygen. The animal was placed in a dorsal recumbency and, following surgical preparation, the left stifle joint opened via a lateral parapatellar approach. Following patella subluxation, a full thickness chondral defect 8 mm diameter were produced on the weight bearing surface of the medial femoral condyle using a punch biopsy and curette. Care was taken to ensure that the calcified cartilage was removed from the subchondral bone and that the edge of the defect was perpendicular to the subchondral bone. Following creation of the defect 6 microfracture holes were produced in the defect using a micropick. These microfracture holes passed through the subchondral bone plate. Following creation of the microfracture, in those groups that received the treatment, a Chondro-Gide™ membrane loaded with the appropriate amount of rhFGF-18 was glued to the chondral defect using Tisseal Fibrin glue and the joint closed in a standard fashion.

For animals treated i.a., 30 ng/ml rhFGF-18 was injected into the medial femoro-tibial joint once a week for 3 weeks. Animals that received one cycle of rhFGF-18 had injections at 4, 5 and 6 weeks post-operatively; animals that received two cycles of rhFGF-18 had injections at 4, 5 and 6 weeks and 16, 17 and 18 weeks post-operatively. All animals were sacrificed at 6 months post surgery.

TABLE 1

Experimental Groups

| Group | Treatment |
|-------|-----------|
| A | Control, intra-articular injection of carrier vehicle |
| B | Intra-articular (i.a.) injection of rhFGF-18 - 2 cycles |
| C | Control |
| D | Membrane alone |
| E | Membrane + 0.064 µg total dose rhFGF-18 |
| F | Membrane + 0.64 µg total dose rhFGF-18 |
| G | Membrane + 6.4 µg total dose rhFGF-18 |
| H | Membrane + 32 µg total dose rhFGF-18 |

Results—Gait Analysis

Figure 1A:
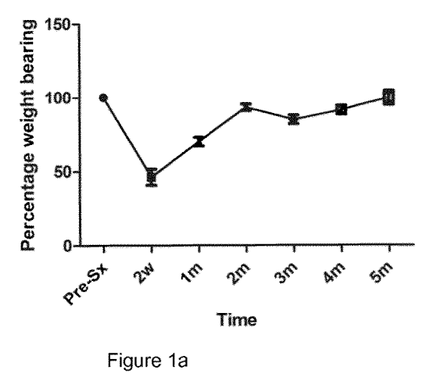
FIG. 1a. Percentage weight bearing of control group sheep.

In the control group (FIG. 1a) there was a marked decrease in weight bearing after surgery and then a slow increase in weight bearing on the operated limb over time. Weight bearing back to pre-surgery levels was achieved by 2 months i.e. no statistical difference exists between the values recorded pre-surgery and 2, 3, 4 and 5 months.

Figure 1B:
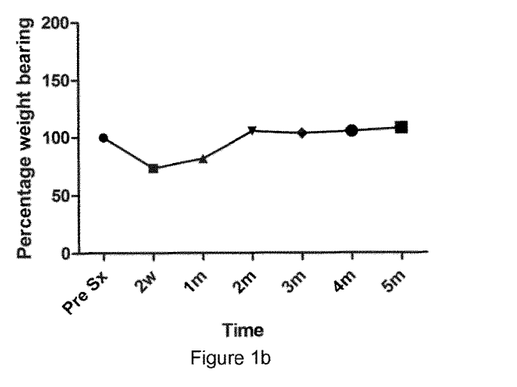
FIG. 1b. Percentage weight bearing of group treated with intra-articular FGF-18.

In group B (FIG. 1b) there was a significant increase in weight bearing after surgery compared to the control (control mean 46.3+\−23.63 compared to group B mean 73.4+\−13.7) (t test $p<0.0001$) and then a slow increase in weight bearing on the operated limb over time. There was a statistically significant ($p<0.05$) difference in the weight bearing after surgery compared to that detected at 1 m. No other significance could be detected. Weight bearing back to pre-surgery levels was achieved by 2 months i.e. no statistical difference exists between the values recorded pre-surgery and 2, 3, 4 and 5 months.

Figure 1C:
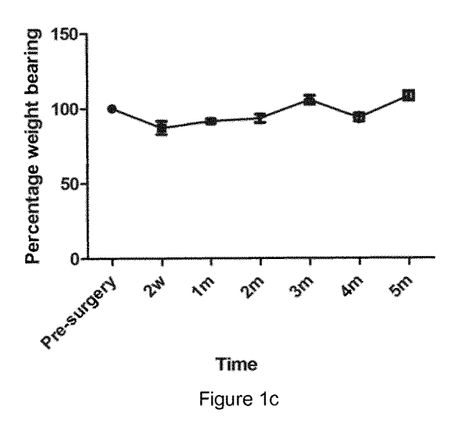
FIG. 1c. Percentage weight bearing of group treated with 32 μg rhFGF-18 applied on a Chondri-Gide membrane at the point of surgery.

In contrast to the control and intra-articular rhFGF-18 groups, in group H, no significant differences were detected between weight bearing prior to surgery and post-surgery (FIG. 1c) i.e. it was not possible to detect that the animals had received any surgical intervention during this time frame. This was significantly different from the reduction in weight bearing detected at 2 w post-surgery in all other groups measured.

Figure 1D:
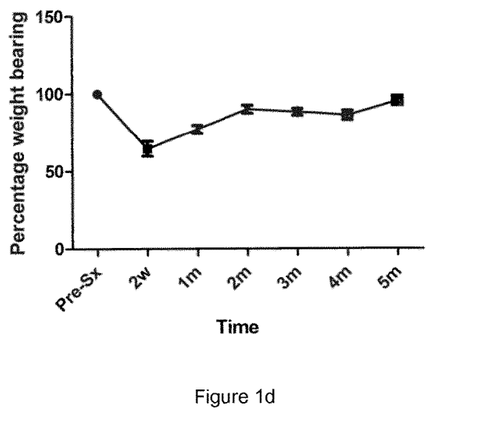
FIG. 1d. Percentage weight bearing of group treated with 6.4 μg rhFGF-18 applied on a Chondri-Gide membrane at the point of surgery.
Figure 2:
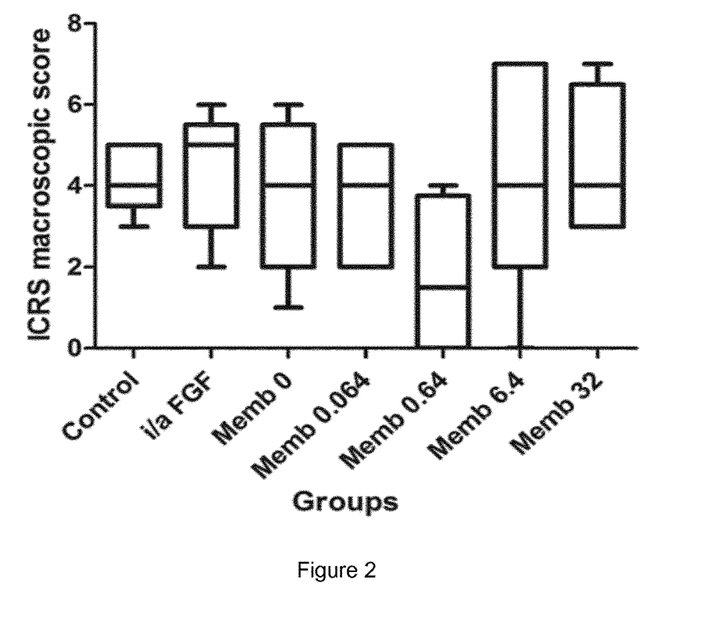
FIG. 2. The effect of rhFGF-18 on the total ICRS score.

In group G, weight bearing post surgery returned to levels not significantly different to pre-surgery levels by 2 months (FIG. 1d), although there was a similar trend noted to that seen in the higher dose of rhFGF-18/membrane.

Results—Gross Morphology

The effect of rhFGF-18 on the gross morphology of the healed tissue was quantified using the ICRS score (Table 3). There were no statistically significant differences in the gross histology of the lesions as measured by the ICRS gross morphology scoring system. Individual analysis of the components of the ICRS morphology score did not identify a component that had any statistically significant results. These results indicate that the addition of 32 µg rhFGF-18 applied on a Chondri-Gide membrane at the point of surgery leads to a significant reduction in post-operative pain at 2 weeks post-surgery, as assessed using a force plate. No other significant differences were detected.

Results—Stiffness

Figure 3:
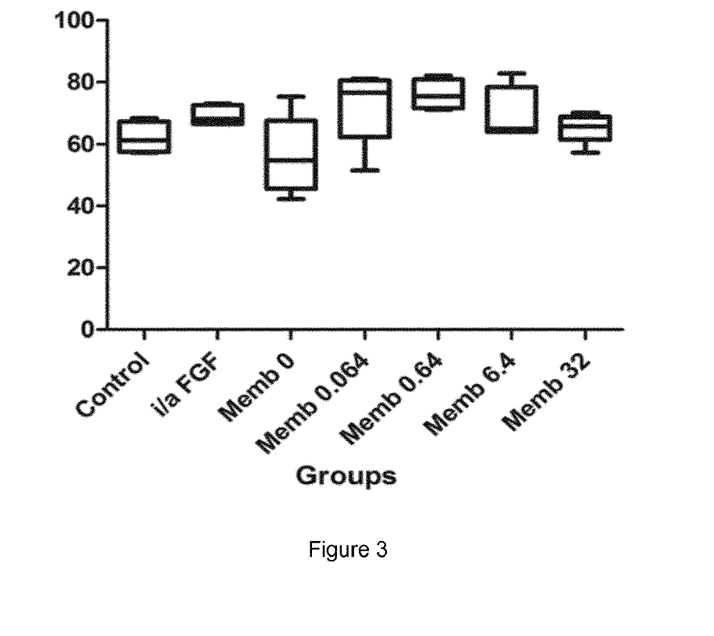
FIG. 3. The effect of rhFGF-18 on the stiffness of the repair cartilage.

Stiffness measurements were taken from the chondral defect and the corresponding site in the other, unoperated limb using a handheld digital durometer (Shore S1, M scale, Instron Ltd, UK) (FIG. 3). No significant differences were present between groups. In this experiment we are aiming for a restoration of the mechanical stiffness of the operated cartilage to match the control cartilage. Therefore no significant difference between operated and unoperated limb is the desired outcome.

Results—Histology

Figure 4:
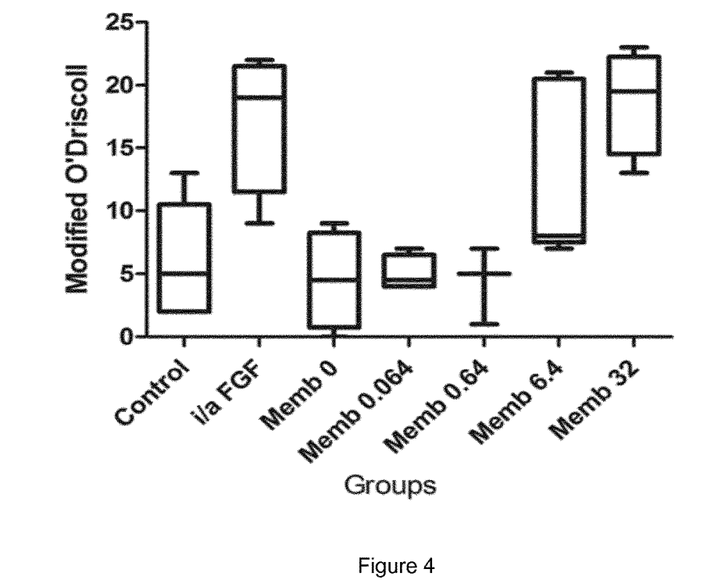
FIG. 4. Effect of rhFGF-18 on the Modified O'Driscoll score.

The quality of the histological repair within the lesion and the adjacent tissue was quantified using the modified O'Driscoll score (FIG. 4). No significant differences were detected with a Kruskal-Wallis test. In order to assess the data differently a one way ANOVA was performed with a post-hoc Tukey's test. Both control groups (Groups A and C) had means that were not statistically significantly different, as would be expected. As has been shown in previous studies, the administration of two cycles of i.a. rhFGF-18 significantly improved the modified O'Driscoll score. In addition, there was a statistically significant increase in modified O'Driscoll score when both 6.4 µg and 32 µg rhFGF-18 were loaded onto the Chondro-Gide™ membrane. There was no difference between the intra-articular injected FGF-18 and 32 µg rhFGF-18 loaded onto the membrane at the point of surgery.

Results—Sub-Analysis of the Modified O'Driscoll Score

Sub-analysis of the components of the modified O'Driscoll score was performed in order to identify specifically which histological parameters were and were not affected by the inclusion of rhFGF-18. When all data was included, no statistically significant differences were detected in any of the individual components of the scoring system.

Results—Immunohistochemistry (IHC)

IHC for collagen types I, II and VI was performed. This demonstrated that the repair tissue produced in the control samples was predominantly mixed hyaline/fibrocartilage (type I and II collagen IHC, with little organized type VI collagen staining). In contrast, in the presence of rhFGF-18 the repair tissue was type II collagen positive with clear pericellular type VI collagen staining indicating a mature hyaline cartilage repair where present. These results indicate that the addition of two cycles of rhFGF-18 intra-articularly post surgery or 32 µg rhFGF-18 delivered on a Chondri-Gide™ membrane at the point of surgery leads to a significant improvement in the modified O'Driscoll score. Histology demonstrates that the repair tissue produced in the presence of these rhFGF-18 delivery systems is type II and VI collagen positive i.e. is hyaline cartilage, compared to a mixed hyaline/fibrocartilage tissue produced in the controls and in animals treated with lower dose rhFGF-18 delivered on the membrane at the point of surgery Conclusions In this study we have demonstrated that the inclusion of 32 µg rhFGF-18 delivered on a Chondro-Gide™ membrane at the point of surgery significantly reduced post-operative pain 2 weeks post surgery (compared to controls, lower doses of rhFGF-18 applied on the membrane and intra-articular rhFGF-18), significantly improved the modified O'Driscoll score compared to controls and lower doses of rhFGF-18 applied on the membrane, and had an equivalent modified O'Driscoll score compared to intra-articular rhFGF-18. These results, albeit with very small numbers of animals, indicate that the application of rhFGF-18 on a Chondro-Gide™ membrane is an effective treatment of chondral defects treated by microfracture.

Example 2: Collagen/GAG Scaffold Comprising rhFGF-18

Method

Osteochondral defects (5.8×6 mm) were created in the medial femoral condyle (MFC) and the lateral trochlear sulcus (LTS) of the right stifle joint of 24 skeletally mature Welsh Mountain sheep. Defects were either left empty (Control; group A) or filled with a 6×6 mm collagen/GAG scaffold (a Chondromimetic scaffold), either on its own (scaffold only; control; group B) or in combination with rhFGF-18 (30 µg, group C) or BMP-7 (100 µg; group D) (n=6 for each group) (see Table 2). At 6 months the sheep were humanely euthanized, at which time the repair tissue underwent non destructive mechanical testing, gross assessment with the ICRS repair score, and was assessed for the presence of degenerative change. This was followed by histological and immunohistochemical analysis looking at the cartilage specific markers of proteoglycan (Safranin O/fast green), and types I, II and VI collagens. Sections were scored using the semi-quantitative Modified O'Driscoll score. Statistical analysis included one way ANOVA and post-hoc testing with Bonferroni's correction with $p<0.05$ set as the level of significance.

Chondromimetic (Orthomimetics Ltd) is a scaffold composed of type I bovine collagen and chondroitin-6-sulphate glycosaminoglycan (collagen/GAG scaffold).

TABLE 2

| Experimental Groups | |
| --- | --- |
| Group | Treatment |
| A | Defects left empty |
| B | Control, scaffold alone |
| C | Scaffold + rhFGF-18 30 µg |
| D | Scaffold + BMP-7 100 µg |

Results—Gross Morphology

Figure 5:
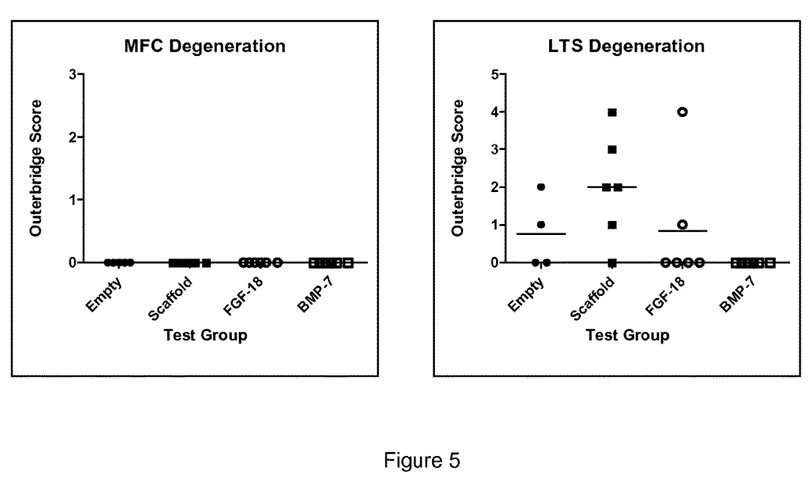
FIG. 5. Degenerative change in the MFC and LTS ($p=0.0381$) at necropsy.

None of the animals showed any signs of infection after surgery. Degenerative change was seen in many animals in the LTS, particularly in the control groups (FIG. 5). This would likely be as a result of the lateral parapatellar approach, with resultant alteration in patellofemoral biomechanics. Non-parametric analysis showed a statistically significant difference between the degeneration in the BMP-7 group compared with the scaffold only (p=0.0381).

Results—Cartilage Repair Score

Figure 6:
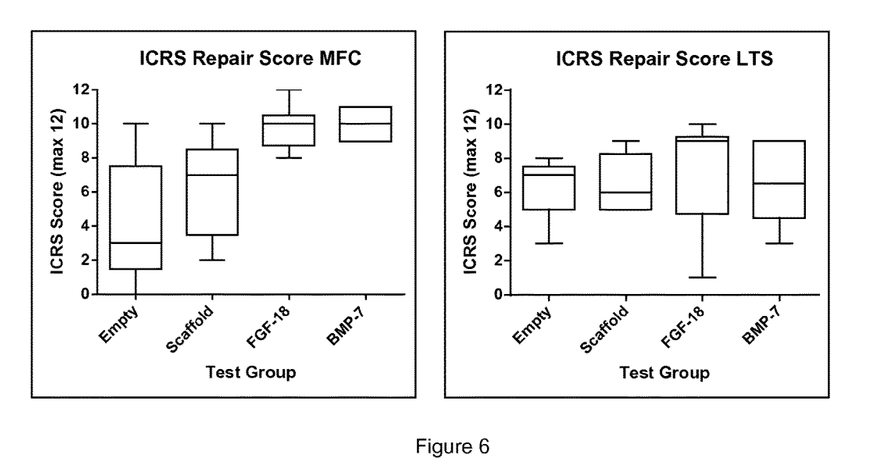
FIG. 6. International Cartilage Repair Society gross repair score of MFC ($p=0.0015$) and LTS ($p>0.05$).

All animals were scored by one observer, who was blinded to the treatment group. FIG. 6 shows the distribution of scores between groups. Both FGF-18 and BMP-7 had significantly improved ICRS repair scores in the MFC compared to empty defects (p<0.05). A trend toward improved repair is seen with both growth factors in comparison to the scaffold only but no statistically significant difference existed between groups (p>0.05). Much greater variability is seen between the controls than growth factors in the MFC; however the reverse is true in the LTS.

Results—Mechanical Testing

Figure 7:
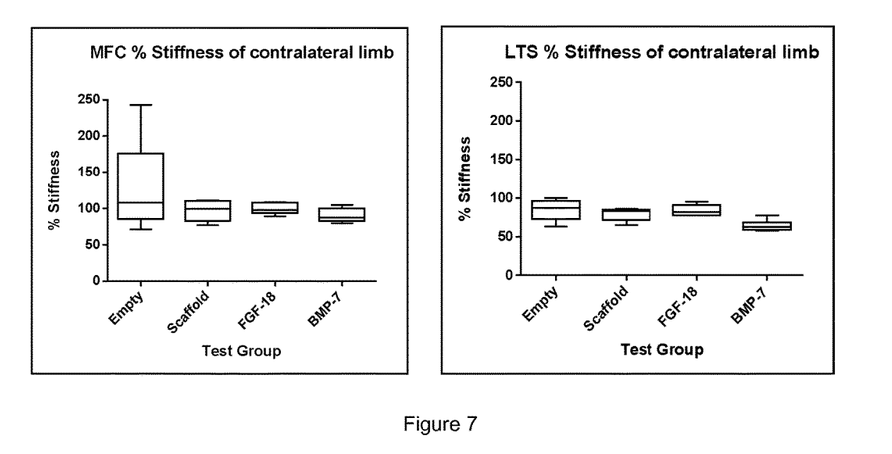
FIG. 7. Stiffness measurements of the defects in the MFC ($p>0.05$) and LTS ($p=0.0033$) expressed as percentage measurements of the contralateral limb.
Figure 8:
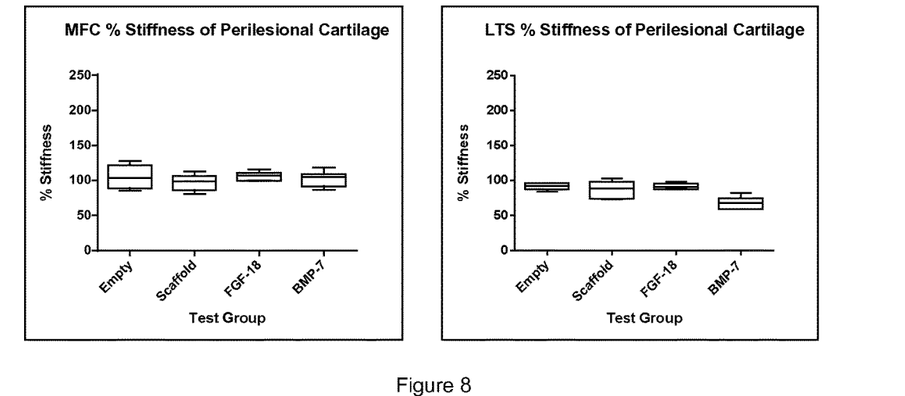
FIG. 8. Stiffness measurements of the defects in the MFC ($p>0.05$) and LTS ($p=0.0002$) expressed as percentage measurements of the perilesional cartilage.

Repeated measurements were taken by one observer using the Shore S1 digital durometer (Instron). In the MFC (FIG. 7), no differences existed between the treatment groups in the mean percentage stiffness of the contralateral limb (p=0.31) nor of the perilesional cartilage (p=0.573). In the LTS (FIG. 8), BMP-7 was significantly less stiff than both rhFGF-18 and the empty defect when compared to the cartilage of contralateral limb (p=0.0033), and less stiff than both the scaffold only and rhFGF-18 when compared to its perilesional cartilage (p=0.0002) (p<0.05 for all post hoc analysis).

Results—Histology and Immunohistochemistry

Control Group A=Empty Defects (Pictures not Shown):

Good tissue fill in the empty defects were generally seen throughout all animals. In the majority of defects, an advancement of the tidemark with a thin cartilage layer was seen. Positive Safranin O staining was seen in all MFC defects with relatively poor staining in the LTS. All defects showed positive type I collagen staining with some staining positive for type II collagen. No defects stained positive for pericellular type VI collagen. These observations indicate that a fibrocartilage repair was present in the defect, with many showing a fibrous repair tissue.

Control Group B=Scaffold Only (Pictures not Shown):

Good lateral integration was seen in all defects. Attempts at regeneration of the articular cartilage were seen particularly in the MFC, with chondrocytes in lacunae arranged in columns in the deep zone, with more flattened chondrocytes in the superficial zone. This was seen mostly in the lateral margins, with disorganised tissue often found centrally. A recurring trend was the presence of a cleft or fissure located centrally in the chondral layer in four of six MFC defects, and residual scaffold in the deep aspect of all defects. However, this residual scaffold did show new connective tissue within the porous structure and new material being laid down on the struts. The sections show moderate Safranin O staining with a mixed picture of type I and II collagen staining. A degree of type VI pericellular staining was seen, again in the lateral margins, with mostly inter-territorial matrix staining centrally. These findings are suggestive of a fibrocartilage repair with some areas of hyaline cartilage-like features, particularly in the lateral margins.

FGF-18 Treated Group C (Pictures not Shown):

All defects showed good subchondral bone regeneration, with many being observed to have remaining scaffold in situ. No defects had cystic formation. A cleft was commonly seen in the centre of the defect extending down into the middle of the defect often communicating with the scaffold. The thickness of the cartilage layer had been recreated in five of six MFC defects and two of six LTS defects, especially laterally, where excellent integration with host cartilage existed and the tissue mostly resembled hyaline cartilage architecture. A more fibrocartilagenous tissue repair was often seen more centrally. Generally excellent Safranin O staining was present throughout the defects indicating good proteoglycan production. In the best cases there was negative type I collagen staining with positive type II and pericellular collagen type VI staining indicative of repair tissue closely resembling hyaline cartilage. Generally, repair tissue with areas highly suggestive of hyaline cartilage was observed to be mixed with good quality fibrocartilage.

BMP-7 Treated Group D (Pictures not Shown):

Poor defect fill was seen in four of the six LTS defects with very poor Safranin O staining in the other two defects. The lateral integration was moderate at best with poor integrity of the fibrocartilage tissue and in adjacent native tissue. In the MFC, the proteoglycan deposition was improved as seen by increased Safranin O staining; however the thickness of the cartilage layer is mostly reduced in comparison to the native cartilage. Two of the six MFC defects were associated with large subchondral cysts. These were found to be walled off cysts, not seemingly communicating with the joint surface, lined with chronic inflammatory cells. Only a small amount of scaffold was associated with the cysts. At best, fibrocartilage is observed with positive staining for both type I and II collagens. No sections exhibited normal pericellular type VI collagen staining. Residual scaffold was observed in the majority of defects in the MFC compared to the LTS. A greater number of cysts were found in the MFC associated with BMP-7 than any of the other treatment groups, both of which were large.

Results—Semi Quantitative Analysis of Histology Sections

Figure 9:
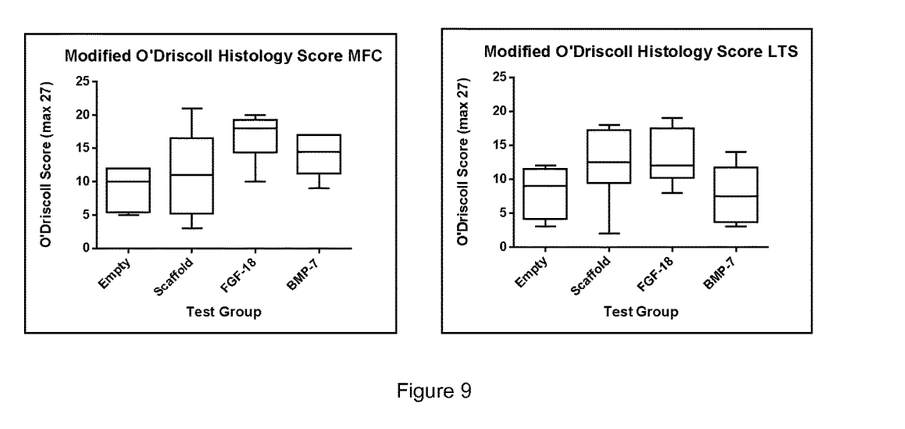
FIG. 9. The modified O'Driscoll score for both MFC ($p=0.0390$) and LTS ($p>0.05$) showing comparison between groups.

All of the Safranin O/fast green sections were scored using the Modified O'Driscoll histology score by one blinded observer who was an expert in analysing articular cartilage repair. A significant improvement was seen in the rhFGF-18 group in the MFC when compared to the empty defect (p=0.0390) (FIG. 9). A similar trend was observed in the LTS; however, no statistical significance was reached. Interestingly, the BMP-7 group showed the worst results of all in the LTS with a wide variability.

Conclusions

Based upon the results of this study, we can conclude that rhFGF-18, when combined with Chondromimetic scaffold in an ovine osteochondral defect model, produces a superior repair tissue to scaffold alone or BMP-7 combined with Chondromimetic scaffold.

Encompassed by the invention is:

1) A substance delivery system comprising at least one polymeric material forming a matrix and an anabolic drug.

2) The substance delivery system according to 1), wherein the matrix is a scaffold or a membrane.

3) The substance delivery system according to 2), wherein the scaffold is a biphasic scaffold or wherein the membrane is a bilayered membrane.

4) The substance delivery system according to any one of 1) to 3), wherein the at least one polymeric material is collagen.

5) The substance delivery system according to any one of 1) to 3), wherein the at least one polymeric material is a combination of collagen and glycosaminoglycan (GAG).

6) The substance delivery system according to any one of 1) to 5), which further comprises chondrogenic cells.

7) The substance delivery system according to any one of 1) to 6), wherein the anabolic drug is an FGF-18 compound.

8) The substance delivery system according to 7), wherein the FGF-18 compound is selected from the group consisting of: a) a polypeptide comprising or consisting of the human FGF-18 mature form comprising residues 28-207 of SEQ ID NO:1, or b) a polypeptide comprising or consisting of SEQ ID NO:2.

9) A process for producing the substance delivery system according to any one of 1) to 8), which comprises the steps of: a) preparing a matrix comprising at least one polymeric material, and b) adding the anabolic drug to the matrix prepared in step a).

10) The process according to 9) which further comprises the step c) adding chondrogenic cells to the matrix prepared in step a).

11) A substance delivery system according to any one of 1) to 8) for use in the treatment of a cartilage disorder.

12) The substance delivery system for use according to 11), wherein the cartilage disorder is selected from osteoarthritis, cartilage injury and osteochondral defects.

13) The substance delivery system for use according to 11) or 12), wherein the substance delivery system is administered to a patient in need of said treatment via a transplantation procedure.

14) An article of manufacture comprising the substance delivery system according to any one of 1) to 8).

15) The article of manufacture according to 14), wherein each of the components are combined either before implantation or after implantation.

Tables

TABLE 3

Scoring Criteria using the ICRS score to assess the healing of the chondral defect.

| Characteristic | Grading | Score |
|---|---|---|
| Degree of defect repair | Level with surrounding cartilage | 4 |
| | 75% repair of defect depth | 3 |
| | 50% repair of defect depth | 2 |
| | 25% repair of defect depth | 1 |
| | 0% repair of defect depth | 0 |
| Integration to border zone | Complete integration with border zone | 4 |
| | Demarcating border <1 mm | 3 |
| | ¾ of graft integrated, ¼ with notable border >1 mm | 2 |
| | ½ of graft integrated with surrounding cartilage, ½ with a notable border >1 mm | 1 |
| | From no contact to ¼th of graft integrated with surrounding cartilage | 0 |
| Macroscopic appearance | Intact smooth surface | 4 |
| | Fibrillated surface | 3 |
| | Small, scattered fissures or cracks | 2 |
| | Several, small or few but large fissures | 1 |
| | Total degeneration of grafted area | 0 |
| Total | | 12 |

TABLE 4

Modified O'Driscoll Histology Score

| | Characteristic | | Grading | Score |
|---|---|---|---|---|
| I | % Hyaline Cartilage: | | 80-100 | 8 |
| | | | 60-80 | 6 |
| | | | 40-60 | 4 |
| | | | 20-40 | 2 |
| | | | 0-20 | 0 |
| II | Structural Characteristics: | A. Surface Irregularity: | Smooth and intact | 2 |
| | | | Fissures | 1 |
| | | | Severe disruption, fibrillation | 0 |
| | | B. Structural integrity: | Normal | 2 |
| | | | Slight disruption, including cysts | 1 |
| | | | Severe lack of integration | 0 |
| | | C. Thickness: | 100% of normal adjacent cartilage | 2 |
| | | | 50-100% or thicker than normal | 1 |
| | | | 0-50% | 0 |

TABLE 4-continued

Modified O'Driscoll Histology Score

| | Characteristic | Grading | Score |
|---|---|---|---|
| | D. Bonding to adjacent cartilage: | Bonded at both ends of graft | 2 |
| | | Bonded at one end/ partially both ends | 1 |
| | | Not bonded | 0 |
| III | Freedom from cellular changes of degeneration: | Normal cellularity, no clusters | 2 |
| | | Slight hypocellularity, <25% chondrocyte clusters | 1 |
| | | Moderate hypocellularity, >25% clusters | 0 |
| IV | Freedom from degenerate changes in adjacent cartilage: | Normal cellularity, no clusters, normal staining | 3 |
| | | Normal cellularity, mild clusters, moderate staining | 2 |
| | | Mild or mod hypocellularity, slight staining | 1 |
| | | Severe hypocellularity, slight staining | 0 |
| V | Reconstitution of subchondral bone: | complete reconstitution | 2 |
| | | greater than 50% recon | 1 |
| | | 50% or less recon | 0 |
| VI | Bonding of repair cartilage to denovo subchondral bone: | complete and uninterrupted | 2 |
| | | <100% but >50% recon | 1 |
| | | <50% complete | 0 |
| VII | Safrinin O staining: | >80% homogenous positive stain | 2 |
| | | 40-80% homogenous positive stain | 1 |
| | | <40% homogenous positive stain | 0 |
| | TOTAL SCORE | | Max 27 |

REFERENCES

1. Ellsworth et al., 2002, Osteoarthritis and Cartilage, 10: 308-320
2. Shimoaka et al., 2002, JBC 277(9):7493-7500
3. WO2008023063
4. WO2004032849
5. WO2012172072
6. Ringe J. et al., 2012, Nature Reviews Rheumatology 8(8): 493-498
7. J. K. Tessmar, A. M. Gopferich, 2007, Adv. Drug Delivery Rev. 59:274-291
8. Power J. et al., 2014, Journal of Orthopaedic Research, epublication on Jan. 16, 2014
9. Yun Y-R et al., 2010, J. Tissue Eng. 1:1-18
10. WO98/16644
11. WO2006/063362
12. Custers et al., 2007, Osteoarthritis and Cartilage, 15:1241-1248

The invention claimed is:

1. A substance delivery system comprising at least one polymeric material forming a matrix and an anabolic drug, wherein the at least one polymeric material comprises collagen and wherein said anabolic drug is included in the at least one polymeric material forming the matrix, wherein the matrix is a biphasic scaffold or a biphasic membrane, and wherein the anabolic drug is an FGF-18 polypeptide comprising SEQ ID NO: 1 or a fragment thereof having chondrocyte or osteoblast proliferation activity or cartilage formation activity, and wherein the anabolic drug is present at a dose from 20 to 100 mcg/system.

2. The substance delivery system according to claim 1, wherein the at least one polymeric material is a combination of collagen and glycosaminoglycan (GAG).

3. The substance delivery system according to claim 1, which further comprises chondrogenic cells.

4. The substance delivery system according to claim 1, wherein the FGF-18 polypeptide is selected from the group consisting of:
   a) a polypeptide comprising residues 28-207 of SEQ ID NO:1, and
   b) a polypeptide comprising SEQ ID NO:2.

5. A process for producing the substance delivery system according to claim 1, which comprises the steps of: a) preparing the matrix comprising at least one polymeric material, and b) adding the anabolic drug to the matrix prepared in step a), wherein said anabolic drug is included in the at least one polymeric material forming the matrix.

6. The process according to claim 5 which further comprises a step c) of adding chondrogenic cells to the matrix prepared in step a).

7. A method of treating a cartilage damage comprising administering the substance delivery system of claim 1 to a subject in need of treatment.

8. The method according to claim 7, wherein the cartilage damage is due to a cartilage disorder i& selected from osteoarthritis, cartilage injury and osteochondral defects.

9. The method according to claim 7, wherein the substance delivery system is administered to a patient in need of said treatment via a transplantation procedure.

10. An article of manufacture comprising the substance delivery system according to claim 1.

11. The article of manufacture according to claim 10, wherein each of the components are combined either before implantation or after implantation.

* * * * *

UNITED STATES PATENT AND TRADEMARK OFFICE
CERTIFICATE OF CORRECTION

| | | |
|---|---|---|
| PATENT NO. | : 10,086,112 B2 | Page 1 of 1 |
| APPLICATION NO. | : 15/120137 | |
| DATED | : October 2, 2018 | |
| INVENTOR(S) | : Christoph H. Ladel and Hans Guehring | |

It is certified that error appears in the above-identified patent and that said Letters Patent is hereby corrected as shown below:

In the Specification

<u>Column 1,</u>
Line 52, "(i.e.)" should read --(i.a.)--.

In the Claims

<u>Column 20,</u>
Line 51, "disorder i& selected" should read --disorder selected--.

Signed and Sealed this
Twenty-seventh Day of August, 2019

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 207
<212> TYPE: PRT
<213> ORGANISM: Homo sapiens
<220> FEATURE:
<223> OTHER INFORMATION: human FGF-18
```

<400> SEQUENCE: 1

```
Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
        50                  55                  60

His Ile Gln Val Leu Gly Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
                100                 105                 110

Lys Gly Lys Leu Val Gly Lys Pro Asp Gly Thr Ser Lys Glu Cys Val
            115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
            195                 200                 205
```

<210> SEQ ID NO 2
<211> LENGTH: 170
<212> TYPE: PRT
<213> ORGANISM: Artificial
<220> FEATURE:
<223> OTHER INFORMATION: recombinant truncated FGF-18(sprifermin)

<400> SEQUENCE: 2

```
Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
            20                  25                  30

Ser Arg Thr Ser Gly Lys His Ile Gln Val Leu Gly Arg Arg Ile Ser
        35                  40                  45

Ala Arg Gly Glu Asp Gly Asp Lys Tyr Ala Gln Leu Leu Val Glu Thr
    50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
        115                 120                 125

Lys Lys Gly Arg Pro Arg Lys Gly Pro Lys Thr Arg Glu Asn Gln Gln
    130                 135                 140
```

-continued

```
Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165             170

<210> SEQ ID NO 3
<211> LENGTH: 139
<212> TYPE: PRT
<213> ORGANISM: artificial
<220> FEATURE:
<223> OTHER INFORMATION: recombinant BMP-7 (Eptotermin alfa)

<400> SEQUENCE: 3

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```